United States Patent [19]

Molina

[11] 4,269,068

[45] * May 26, 1981

[54] ULTRASONIC COUPLANT COMPOSITIONS AND METHOD FOR EMPLOYING SAME

[75] Inventor: Orlando G. Molina, Westminster, Calif.

[73] Assignee: Rockwell International Corporation, El Segundo, Calif.

[*] Notice: The portion of the term of this patent subsequent to Sep. 20, 1994, has been disclaimed.

[21] Appl. No.: 604,407

[22] Filed: Aug. 13, 1975

Related U.S. Application Data

[63] Continuation-in-part of Ser. No. 444,432, Feb. 21, 1974, Pat. No. 3,915,885, and a continuation-in-part of Ser. No. 444,433, Feb. 21, 1974, Pat. No. 3,915,886, and a continuation-in-part of Ser. No. 521,730, Nov. 7, 1974, Pat. No. 3,939,092, and a continuation-in-part of Ser. No. 535,262, Dec. 23, 1974, Pat. No. 3,981,185, and a continuation-in-part of Ser. No. 580,442, May 23, 1975, Pat. No. 4,049,568.

[51] Int. Cl.$^3$ .................... C09K 3/00; G01N 29/04
[52] U.S. Cl. ........................... 73/644; 73/104; 252/301.19; 252/408; 252/DIG. 1; 252/DIG. 6
[58] Field of Search ................. 73/67.5 R, 67.6, 67.7, 73/67.8 R, 67.8 S, 67.9, 71.5 US, 104, 644; 252/301.2 P, 408, 408 R, 301.19

[56] References Cited

U.S. PATENT DOCUMENTS

| | | | |
|---|---|---|---|
| 2,870,220 | 1/1959 | Carter | 260/615 B |
| 3,504,041 | 3/1970 | Weipert | 252/89 X |
| 3,826,127 | 7/1974 | Molina | 73/67.5 R |

Primary Examiner—Richard D. Lovering
Attorney, Agent, or Firm—Charles T. Silberberg; Max Geldin

[57] ABSTRACT

Biodegradable water washable composition in the form of a gel for use in non-destructive ultrasonic inspection of surface and subsurface flaws and discontinuities in bodies, and which is stable and heat resistant, such composition consisting essentially of a (1) a surfactant comprised of certain straight chain, primary, aliphatic oxyalkylated alcohols, particularly biodegradable surfactants comprised of the nonionic condensation products of linear aliphatic alcohols having from 10 to 18 carbon atoms, with ethylene oxide and propylene oxide, preferably in the form of a mixture thereof, such as the material marketed as Plurafac A-24, or in the form of certain ethoxylated secondary alcohols, particularly the biodegradable nonionic surfactants comprised of ethoxylates of a mixture of secondary alcohols having linear alkyl chains of from 11 to 15 carbon atoms, and (2) silica, particularly fumed silica, such silica employed e.g. in a proportion of about 15% by weight of the composition.

The composition or gel is applied to a surface of a body such as a metal aircraft structural part, and a probe or transducer of an ultrasonic testing device is contacted or pressed against the gel, and the transducer is caused to move or slide in various directions on the gel to transmit ultrasonic energy through the gel and the object, to inspect the object and locate any surface or subsurface flaws or discontinuities.

27 Claims, No Drawings

ULTRASONIC COUPLANT COMPOSITIONS AND METHOD FOR EMPLOYING SAME

This application is a continuation-in-part of my copending applications Ser. Nos. 444,432 and 444,433, both filed Feb. 21, 1974, now U.S. Pat. Nos. 3,915,885 and 3,915,886; 521,730, filed Nov. 7, 1974, now U.S. Pat. No. 3,939,092; 535,262 filed Dec. 23, 1974, now U.S. Pat. No. 3,981,185; and 580,442, filed May 23, 1975, now U.S. Pat. No. 4,049,568.

BACKGROUND OF THE INVENTION

This invention relates to the inspection of surface and subsurface flaws and discontinuities in objects by ultrasonic nondestructive testing, and is particularly concerned with the provision of a novel improved ultrasonic couplant composition having a minimum of components to provide good ultrasonic transmission and particularly adapted for use for such ultrasonic inspection, such composition being biodegradable, stable and heat resistant; and also to a method of ultrasonic inspection employing such novel composition.

Ultrasonic nondestructive testing of bodies such as metal parts has been developed. This is a method which utilizes UHF (ultra-high frequency) sound waves to detect discontinuities in parts. An ultrasonic testing device is employed, in which a probe or transducer is placed in contact with a surface of the part to be inspected. Ultrasonic waves are generated by applying a pulsed oscillating voltage from a pulser to a transducer (piezoelectric crystal). When the transducer is electrically excited and is adequately coupled to a part being inspected, an ultrasonic wave passes into the part. A change in acoustic properties of the part (surface and subsurface cracks, discontinuities, part surfaces, interfaces) reflects the wave back to the transducer. The reflected wave mechanically stresses the transducer and the transducer generates electrical charges. The electrical signals are applied to an amplifier circuit with the ultrasonic instrument, where they are amplified and displayed on a CRT (cathode-ray tube).

In the above procedure, a couplant is required to be applied to a surface of the object to be tested, to provide an effective medium for ultrasonic transmission between the transducer or probe applied to the surface of the body, and the body undergoing nondestructive testing. Thus, the primary purpose of couplants is to provide a suitable ultrasonic path between the transducer and part being inspected. Air is a poor conductor of ultrasonic energy. The couplant also fills in and smooths out irregularities of a part's surface and aids in movement of the transducer. A further purpose of the couplant is to serve as an acoustic impedance matching medium. The closer the couplant acoustic impedance matches that of the part being inspected, the better the ultrasonic wave transfer.

Ultrasonic coupling compositions which have been employed to date by the industry include for example, water, glycerin, light oil and petroleum jelly or grease. These materials have been used in the past basically because of their relatively good ultrasonic transmission characteristics. However, none of the prior art couplants such as those noted above have all of the desirable features required for efficient ultrasonic inspection of parts. Thus, for example, water and glycerin are corrosive to certain metals. Oils and greases usually contaminate the surface of the parts to be tested, making it necessary to degrease the parts after testing. Further, in those cases where the parts comprise titanium or its alloys, and degreasing is required, the use of highly flammable solvents which are hazardous, is necessary for this purpose, since the usual chlorinated solvents employed for degreasing are detrimental to titanium and cannot be employed. Also, certain commercially available gelled couplants are unstable and tend to dry up, particularly at elevated temperatures, leaving powdery residues. The odor level of certain prior art couplants also is undesirable.

An additional criterion has recently developed also with respect to ultrasonic couplant compositions. Generally, couplants presently being used and containing solvents and wetting agents present a disposal problem in that they are substantially non-biodegradable, that is, they are very difficult to decompose by bacteria in sewage disposal plants. Hence the necessity for the development of ultrasonic couplant compositions which are biodegradable, that is which employ vehicles which are biodegradable, and are readily available despite the petrochemical shortage, has attained considerable importance.

In my above U.S. Pat. Nos. 3,915,885 and 3,915,886 there is disclosed novel dye penetrant compositions which are biodegradable, containing as the vehicle for the dye, certain biodegradable nonionic oxyalkylated alcohols.

In my U.S. Pat. No. 3,826,127 there is disclosed an improved ultrasonic couplant composition in the form of an aqueous gel containing N-methyl-2-pyrrolidone, a water soluble surfactant, e.g. a nonyl phenyl ether of polyethylene glycol, and silica. Although such couplant composition has been found effective and is stable up to certain elevated temperatures, e.g. of the order of about 125° F., at substantially higher temperatures it loses volatiles and tends to dry out. Also, the patent composition is not biodegradable.

It is accordingly an object of the present invention to provide an ultrasonic couplant composition, that is a composition for use in ultrasonic inspection of parts, having excellent ultrasonic transmission, which is non-corrosive to metals, particularly titanium, aluminum and steel, and their various alloys, is nonflammable, odorless and essentially nontoxic, can be simply applied to a part to be tested and the part surface oriented in a horizontal, vertical or overhead position, without dripping of the composition, and while permitting a probe or transducer to remain adhered to the couplant composition regardless of the orientation of the part surface, such couplant composition being essentially nonhygroscopic, easily removable from the part surface such as by removal with water, and being reusable and relatively inexpensive to manufacture.

Another important object of the present invention is the provision of a biodegradable heat resistant ultrasonic couplant composition which is a simple formulation and which does not require the use of mixtures of conventional solvents and wetting agents, and which is formed of an essentially single or sole vehicle in the form of a biodegradable nonionic surfactant, and which is highly heat stable and does not become powdery at relatively high temperatures. A still further object is the provision of procedure employing such novel heat stable biodegradable ultrasonic couplant composition for inspection of cracks, flaws and metallurgical conditions in structural components, particularly parts heated to elevated temperature.

DESCRIPTION OF THE INVENTION

According to the present invention, it has been found that the above objects and advantages can be accomplished and an improved heat resistant and stable gelled ultrasonic couplant, which is biodegradable, is provided by employing essentially as the sole liquid component or carrier, a surfactant in the form of certain biodegradable nonionic liquid surfactants comprised of certain oxyalkylated linear alcohols, of the types disclosed in my above U.S. Pat. Nos. 3,915,885 and 3,915,886, separately or in admixture, and incorporating silica (silicon dioxide), preferably in powdered form, as gelling agent. Upon incorporation of the powdered silica into the above-noted nonionic surfactant, the resulting composition is essentially in the form of a gel which can range in consistency from thin gels to thick gels, depending particularly upon the proportion of silica incorporated.

The resulting ultrasonic couplant composition or gel of the invention avoids the above noted problems previously encountered in employing ultrasonic couplants on heated surfaces, in that the gel-type compositions of the invention are resistant to liquefaction and decomposition and do not generate fumes when applied to surfaces heated to temperatures, e.g. up to about 300° F. In view of such heat stability, the couplant compositions hereof when applied to slanted or angularly disposed heated surfaces, including vertical heated surfaces, of objects to be nondestructively tested, does not drip, run off or puddle. Moreover, the silica additive is not only heat resistant but is inert with respect to the surfactant component of the couplant composition, and the excess couplant can be readily washed away, the composition other than the inert silica, being biodegradable.

It was unexpected to find that the ultrasonic couplant composition of the invention containing silica is heat resistant at temperatures up to about 300° F. for extended periods of time, whereas the ultrasonic couplant composition of my above patent, and containing particularly N-methyl-2-pyrrolidone as vehicle, is not heat resistant at elevated temperature above about 150° F. and becomes powdery and ineffective under such conditions, while the effectiveness and stability of the couplant composition of the invention on the other hand is not adversely affected by exposure to such elevated temperature use.

The above advantageous characteristics of the couplant composition of the invention are particularly valuable for inspection of parts or components of any equipment which is under continuously highly heated conditions and cannot be shut down conveniently, such as steam generators, atomic reactors, geothermal pressure vessels and piping, or parts with thick cross sections, e.g. welds in shipbuilding, which would require a considerable time for cooling before non-destructive test inspection. Also, the invention composition can be employed on parts which are environmentally heated, such as aircraft in hot climates and parts heated by solar heating. Here, the insulating properties of the couplant gel provide protection to the ultrasonic transducer being used.

The nonionic biodegradable vehicle or carrier employed essentially as the sole liquid vehicle of the ultrasonic couplant composition according to the invention can be alkylene oxide condensation products prepared by the reaction of an organic compound having a reactive hydrogen atom, such as an aliphatic alcohol, with ethylene oxide, propylene oxide, or mixtures thereof.

More particularly, one class of such nonionic vehicles can be defined as straight chain, primary, aliphatic oxyalkylated alcohols, generally in the form of mixtures thereof, wherein the primary aliphatic alcohols can have from 8 to 20 carbon atoms, preferably 10 to 18 carbon atoms, and the oxyalkyl groups are ethylene oxide and propylene oxide, preferably in the form of a mixture thereof.

One class of nonionic vehicles or carriers within the broad class of materials defined above is a cogeneric mixture of compounds represented by the formula:

R—O(A)H wherein: R is an essentially linear alkyl group having from 10 to 18 carbon atoms, with the proviso that at least 70 weight percent of said compounds in said mixture have an R of from 12 to 16 carbon atoms, and A is a mixture of oxypropylene and oxyethylene groups, said oxypropylene and oxyethylene groups being from 55% to 80% of the total weight of the compounds, the oxypropylene to oxyethylene ratio of said total weight being from 0.85:1 to 2.75:1, preferably 1.25:1 to 2.25:1.

Another preferred class of condensation products or oxyalkylated alcohols within the above definition are those wherein the aliphatic alcohols of the oxyalkylated alcohols, or R in the above formula, ranges from 12 to 18 carbon atoms, and the total number of ethylene oxide and propylene oxide groups in the mixture thereof, or designated A in the above formula, ranges from about 4 to about 14.

The term "cogeneric mixture" as employed herein, designates a series of closely related homologues obtained by condensing a plurality of oxide units, with an alcohol or a mixture thereof. As is known, when a mixture of this type is generated, various oxyalkylene chain lengths are obtained.

Alcohols which may be employed in the preparation of the products noted above are those essentially linear, primary, aliphatic alcohols having from 8 to 20 carbon atoms, preferably 10 to 18 carbon atoms. Mixtures of alcohols are usually preferred since their use provides for a good balance of properties in the resulting products. Examples of alcohols are operable include decyl alcohol, undecyl alcohol, lauryl alcohol, tridecyl alcohol, tetra-decyl alcohol, pentadecyl alcohol, cetyl alcohol, heptadecyl alcohol, stearyl alcohol, hydrogenated tallow alcohol, and mixtures thereof. They may be naturally-derived such as from coconut oil or synthetically-derived such as from linear alkanes or linear olefins.

The above nonionic biodegradable surfactants employed as liquid vehicle for the ultrasonic couplant composition according to the invention, are prepared by condensing an alcohol or mixture of alcohols, as described above, with a mixture of ethylene oxide and propylene oxide, in the presence of an alkaline catalyst, such as potassium hydroxide. The oxide mixture may be added to the alcohol in one continuous step or it may be added in several steps. The products thus produced possess random distribution of oxyethylene and oxypropylene groups.

The nonionic surface active agents described above and their method of preparation are disclosed in U.S. Pat. No. 3,504,041, and such disclosure is incorporated herein by reference. These surface active agents are believed to include, for example, that class of surfactants which are marketed as the "Plurafac" surfactants "RA-40" grades.

Another class of biodegradable liquid, water miscible oxyalkylated alcohol condensation products within the above definition are those wherein the aliphatic alcohol, or R, is a straight chain alkyl group having from 8 to 20 carbon atoms, the number of ethylene oxide groups in the mixture thereof with propylene oxide, or A, ranges from 3.75 to 12.75, and the number of propylene oxide groups in such mixture ranges from 1.7 to 7.0, the oxyethylene to oxypropylene ratio in such mixtures being from 1.8:1 to 2.2:1. Such cogeneric mixtures can be prepared in two steps, the first step being condensation of an alcohol mixture and ethylene oxide in the presence of an alkaline condensing agent or catalyst, to form an ethoxylated product, followed by condensing the resulting ethoxylated product with propylene oxide. There can be employed in such reaction a mixture of straight chain aliphatic alcohols having from 8 to 20 carbon atoms in the aliphatic chain. This cogeneric mixture of condensation products and the method of their preparation are disclosed in U.S. Pat. No. 3,340,309, and such disclosure is also incorporated herein by reference. The nonionic oxyalkylated alcohols marketed as the "RA-20" grades of "Plurafac", are believed representative of the class of surface active agents disclosed in the latter patent.

Various other "Plurafac" grades which are marketed and are believed to be generally within the above-described classes of oxyalkylated alcohol surfactants are those designated RA-43, A-24, A-25, B-25-5, B-26 and D-25.

A class of particularly preferred nonionic biodegradable vehicles or carriers which can be employed as substantially the sole liquid vehicle for the ultrasonic couplant compositions according to the present invention are ethoxylates of a mixture of linear secondary aliphatic alcohols, with the hydroxyl groups randomly distributed, the linear aliphatic hydrophobic portion of such alcohols being a mixture of alkyl chains containing in the range from 10 to 17 carbon atoms, preferably from 11 to 15 carbon atoms, and containing an average of from 3 to 12 moles of ethylene oxide.

The above particularly preferred class of nonionic biodegradable surfactant employed as vehicle or carrier for the ultrasonic couplant of the invention is a mixture of compounds which can be represented by the formula:

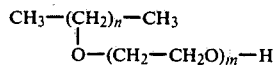

where n is in the range from 9 to 13, and m is an average of 3 to 12.

Although preferably each of the immediately above-defined surfactants is formed of a mixture of two or more linear alkyl hydrophobic chains ranging from $C_{11}$ to $C_{15}$ as noted below, the surfactant can contain a single such chain formed from a single secondary aliphatic alcohol of the types described below.

The linear alkyl hydrophobic portion of the above defined surfactant is a mixture of $C_{11}$ to $C_{15}$ linear alkyl chains, and can be derived from a mixture of $C_{11}$ to $C_{15}$ aliphatic secondary alcohols, for example the secondary undecyl, dodecyl, tridecyl, tetradecyl and pentadecyl alcohols. The hydrophilic portion of the surfactant is a polyoxyethylene chain randomly attached to any carbon atom of the linear alkyl hydrophobic chains, other than to the terminal carbon atoms thereof, through an ether linkage. It will accordingly be understood that the specific carbon atom or —$CH_2$— group in the alkyl hydrophobic chains to which the hydrophilic polyoxyethylene chain is attached will become a

group in the above structural formula. Such hydrophilic polyoxyethylene chain is generally expressed in terms of an average number of moles of ethylene oxide.

Illustrative examples of biodegradable nonionic surfactants of the types defined in the above formula are those consisting of a mixture of ethoxylates of from 11 to 15 carbon atoms in the aliphatic hydrophobic chain, and which have an average of 3, 5, 7, 9 and 12 moles of ethylene oxide, respectively, as the hydrophil.

Materials corresponding to these five examples of biodegradable nonionic surfactants are marketed, respectively as:

| Tergitol | 15-S-3 |
|----------|--------|
| "        | 15-S-5 |
| "        | 15-S-7 |
| "        | 15-S-9 |
| "        | 15-S-12 |

In each case of the Tergitol S series of surfactants listed above, the number to the left of the "S" indicates a hydrophobic aliphatic chain of from 11 to 15 carbon atoms derived from a mixture of alcohols on $C_{11}$ to $C_{15}$ backbone chains, and the number to the right of the "S" designates the average number of moles of ethylene oxide as the hydrophil. Thus for example, Tergitol 15-S-5 is a mixture of linear aliphatic alcohols in the $C_{11}$ to $C_{15}$ range ethoxylated with an average of 5 moles of ethylene oxide. All of these commercially marketed Tergitol S series of surfactants are water soluble except for Tergitol 15-S-3, which is essentially water insoluble. Mixtures of these materials can also be employed in providing the couplant composition of the invention, such as a mixture of the above Tergitols 15-S-5 and 15-S-3; a mixture of 15-S-3 and 15-S-9; and a mixture of 15-S-5 and 15-S-9.

The above preferred class of nonionic biodegradable surfactants employed as vehicle for the gelled couplant composition according to the invention, are prepared by reacting an alcohol or mixture of alcohols, as described above, with the desired proportion of ethylene oxide, in the presence of an alkaline catalyst, such as potassium hydroxide. The ethylene oxide may be added to the alcohol or mixture of alcohols in one continuous step or it may be added in several steps. The products thus produced possess random distribution of oxyethylene groups, as noted above.

Another process for preparing the above preferred nonionic surfactants in the form of ethoxylates of linear secondary aliphatic alcohols, is described in U.S. Pat. No. 2,870,220.

Although Tergitol 15-S-3 is essentially water insoluble and is usually employed in combination with the other members of the Tergitol S series noted above, such as Tergitol 15-S-5, couplant compositions according to the invention containing Tergitol 15-S-3 alone, can be employed. However, Tergitol 15-S-3 has its greatest utility for production of effective couplant compositions according to the invention, when employed in combination with the other water washable and water soluble Tergitols such as Tergitol 15-S-5 and Tergitol 15-S-9. Also, particularly effective couplants are provided according to the invention employing a combination or mixture of the above Tergitols 15-S-5 and 15-S-9, and to which there can be added optionally Tergitol 15-S-3, as described in my above copending application Ser. No. 521,730, now U.S. Pat. No. 3,939,092.

The silica incorporated in the ultrasonic couplant composition is preferably in fine powder form and of particle size ranging from about 0.007 to about 0.050 micron (about 70 to about 500 Angstroms), and is an extremely fluffy, snow-white powder of extremely low bulk density. A commercially available form of this component is marketed as Cab-O-Sil M-5 by Cabot Corporation. The Cab-O-Sil has an enormous external area, one gram of Cab-O-Sil M-5 having about 400 square meters of surface area. Cab-O-Sil M-5 is a submicroscopic fire-dry fumed silica different in structure from precipitated silicas or silica gels, with a maximum density of 2.3 lbs./cu. ft.

The silica thus incorporated into the couplant composition hereof functions when uniformly dispersed in the nonionic surfactant liquid vehicle, to form a colloid dispersion in the gel which provides gel strength and physical integrity, particularly at elevated temperature, e.g. ranging from about 150° to about 300° F. When employed particularly under these conditions the insulating properties of the couplant composition provide protection to the ultrasonic transducer being used.

As previously noted, by addition of the silica, the consistency of the previously highly mobile liquid vehicle or oxyalkylated surfactant changes to a gel-like appearance, with the silica additive holding the liquid vehicle in the location where it is applied, preventing the tendency of the liquid to drip or flow over a vertical or slanted surface.

The amount of silica added to the nonionic liquid surfactant can vary widely, but generally the silica is a substantial portion of the resulting composition, the amount employed being sufficient to convert the nonionic surfactant liquid vehicle into a gel. Generally, however the surfactant is present in major proportion. The amount of silica employed can range from about 4 to about 35%, preferably about 10 to about 25%, by weight of the composition. When smaller proportions of silica are employed within the above noted ranges, the resulting gels can have a thin consistency, and when larger proportions of silica are employed within the above noted ranges, the resulting gels can have a heavy or thick consistency. The gels produced according to the invention are generally clear and transparent or translucent. This is an important feature since after application of the gel to a part surface one can see the surface of the part through the gel. Regardless of the consistency of such gels, it has been found that they are sufficiently adhesive to prevent runoff of the couplant composition when applied to slanted or vertical surfaces, and hold the ultrasonic transducer without assistance from the operator.

It was an unexpected and unique finding that the oxyalkylated nonionic surfactants described above can be gelled by adding the silica, since generally silica does not gel many liquids unless some other liquid such as water or solvents are present. Thus, in the couplant of my above patent containing N-methyl pyrrolidone, water is added to form the aqueous gel matrix.

It is often desirable to be able to check the part surface for the presence of residual gel, after an inspection of the part has been completed and the bulk or major portion of the gel has been removed from the surface. This can be accomplished by incorporating either a daylight visible dye or a fluorescent dye into the gel or couplant composition of the invention and viewing the surface of the part under proper lighting conditions to detect any traces of the gel as indicated by the presence of colored or fluorescent residues imparted by the presence of the dye in the composition. For this purpose, it is preferred to incorporate as an optional component a fluorescent dye which is either colorless or only lightly colored when viewed by visible light, but which provides a bright fluorescent color when viewed under fluorescent or "black" light. Thus the presence of the dye in the gel still renders the gel clear in white or ordinary daylight so that the part surface can be viewed through the layer of gel applied to the part surface.

Various types of fluorescent dyes can be employed including for example the dye marketed as Fluorol 7GA and Morton Fluorescent Yellow G, as well as other fluorescent dyes such as those marketed as Calcofluor Yellow. Azosol Brilliant Yellow 6GF, Rhodanine B, Rhodanine 6GDN, Calcoflour White RW, Blancophor White AW, Auramine and Eosine G. The above-noted Rhodanine dyes, Auramine and Eosine G fluoresce in a color range from greenish yellow to red. There can also be employed non-fluorescent or daylight type dyes such as azo type dyes, e.g. xyleneazo-beta-naphthol, Mefford No. 322 dye, believed to be o-tolueneazoxyleneazo-beta-naphthol, and the azo dyes marketed as Oil Red "O" and Sudan Red. These dyes can be employed where daylight or white light is only available. Here also it is preferred to employ those daylight dyes which are light colored and which permit the gel to be sufficiently transparent to permit viewing the surface of the part to which the gel is applied, through the gel layer or film.

The amount of the optional dye component, e.g. fluorescent or daylight dye, employed, can vary, but it is generally employed in a small amount ranging from about 0.1 to about 5%, preferably about 0.2 to about 2%, by weight of the composition.

Illustrative examples of ultrasonic couplant compositions according to the invention, but not in limitation thereof, are set forth in the table below, the amounts of the respective components being expressed in terms of percent by weight.

COUPLANT COMPOSITIONS
Examples (% by weight)

| Components | 1 | 2 | 3 | 4 | 5 | 6 | 7 | 8 | 9 | 10 |
|---|---|---|---|---|---|---|---|---|---|---|
| Tergitol 15-S-3 | | | | | 20 | | | | | |
| Tergitol 15-S-5 | | | 89.5 | 60 | 60 | | | 93 | | 80 |
| Tergitol 15-S-9 | 84.5 | 85 | | 20 | | | | | 70 | |
| Plurafac A-24 | | | | | | 85 | | | | |
| Plurafac RA-43 | | | | | | | 87.5 | | | |

|Components|1|2|3|4|5|6|7|8|9|10|
|---|---|---|---|---|---|---|---|---|---|---|
|Calcofluor White RW||||0.5||||||
|Fluorol 7GA|0.5||0.5|0.5|||0.5||||
|Morton Fluorescent Yellow G||||||||||2|
|Cab-O-Sil M-5|15|15|10|19|20|15|12|7|30|18|
||100|100|100|100|100|100|100|100|100|100|

In employing the ultrasonic couplant composition or gel according to the invention, for purposes of ultrasonic inspection of a part, the part employed, if necessary, can first be cleaned to remove any contaminants from the part surface. The ultrasonic couplant gel of the invention is readily applied over the surface area of the part to be inspected by ultrasonic transmission through the part. For this purpose the gel can be dispensed and applied to the part surface to provide a thin layer of couplant, by any suitable means such as by the hand, spatula or brush. The probe or transducer of the ultrasonic test equipment is then pressed into contact with the gel on the surface of the part, and is readily moved as by sliding over the gelled surface in any direction necessary for inspection of cracks, flaws, or discontinuities such as part surfaces or interfaces, which may be contained on the surface of the part or within the part. The ultrasonic system for this purpose includes means in the form of a probe or transducer to generate ultrasonic energy, a couplant according to the present invention, and an ultrasonic instrument. The latter instrument contains suitable circuits, including a receiver-amplifier circuit and a CRT for displaying electrical signals generated by the transducer when discontinuity echoes are present, corresponding to any flaws, cracks or discontinuities in the body, as the transducer is moved over the gel on the surface of the body.

The sensitivity of the ultrasonic equipment employed should be such as to be capable of detecting the smallest defect which may be encountered in the part being tested. The thin layer or film of ultrasonic couplant gel of the invention formed on the surface of the part between the probe or transducer and the part surface maintains excellent ultrasonic transmission between the transducer and the part at all times. The presence of cracks, flaws, or discontinuities on the surface or within the body of the part being tested is detected by variations in noise signals received by the testing unit, and which can be indicated on the CRT display mechanism. If there is improper coupling between the transducer and the body being tested, there will be an absence of noise signals received by the test unit. By means of the ultrasonic testing equipment employed, in conjunction with the thin film of gel couplant according to the invention, on the surface of the body, the size of flaws, cracks or discontinuities on or in the test body, for example the length thereof as well as their orientation, can be detected.

The above-described ultrasonic test system and equipment is well known and since it forms no part of the present invention it is not described in detail herein.

After the ultrasonic inspection is completed, the layer or film of couplant composition or gel can be scraped from the surface of the part by suitable means, and returned to the container for reuse. This cannot be done with prior art couplants, particularly when employed at elevated temperatures of the order of about 200°–300° F., since all of such couplants lose volatiles and become powdery. Alternatively, such gel layer can be wiped clean with dry cloths followed by a water moistened wiping. Due to the substantially water soluble nonionic oxyalkylated surfactant contained in the gel, the gel can be readily removed from the part surface by the application of water thereto, as by a water spray, or sprayed mixture of air and water, and the mixture so removed can be discharged to the sewer since it is biodegradable. In such procedure, when the part surface is at high temperature of the order of about 200°–300° F., some of the water wash is converted to steam, which is beneficial. If desired, removal of residual couplant can also be accomplished by washing with volatile-type solvents such as methyl ethyl ketone, acetone or trichloroethane.

Where the ultrasonic couplant composition or gel of the invention contains an optional fluorescent dye component, the surface area of the part from which the gel layer has been removed can be viewed under fluorescent or "black" light illumination to check for the presence of residual or trace amounts of the gel. Any such traces or residual gel will provide bright fluorescent indications, so that a final removal operation of the residual gel can then be performed in those specific areas in which the gel still remains. As previously noted, such excess or residual gel can be removed by water spraying since the gel is highly soluble in water.

Alternatively, in place of employing a fluorescent dye, a dye such as an azo dye which is visible by ordinary white light or daylight can be employed, and any residual gel indicated by any dye smears under ordinary visible light, can then be removed from the part surface in the manner noted above.

As previously indicated, the components of the ultrasonic couplant composition or gel of the invention can be varied, and the amounts thereof varied as described above to provide a formulation which has the desired viscosity for the particular purpose. Preferably, the viscosity of the gel is such that it can be readily applied by means noted above over the part surface to form a thin film or layer of the gel on the surface, and the ultrasonic transducer or probe can be readily moved or can readily slide on the gel surface from one selected area to another. It is particularly noteworthy that in addition to its ability to be readily applied, the ultrasonic couplant gel composition of the invention, due to its viscosity, can be employed on vertical and overhead surface applications without dripping of the composition, and the ultrasonic probe or transducer remains adhered to the gel-treated surface in horizontal, vertical and overhead surface applications, permitting the operator freedom of both hands for example to return to the ultrasonic console of the test equipment and make adjustments, when necessary.

The couplant composition or gel of the invention can be employed for ultrasonic nondestructive testing of all types of parts, whether or not heated to elevated temperature, particularly metal parts of aircraft such as titanium and aluminum wing skins, structural hardware such as bulkheads or wing spars of aircraft, and aluminum, steel or titanium castings. Such ultrasonic testing process employing the couplant composition of the invention can be used to detect so-called "unbonds," e.g. of a fusion welding airplane fuselage bulkhead. Thus the ultrasonic couplant composition of the invention can be employed to detect surface and subsurface flaws and discontinuities, for example cracks, voids and unbonds in the fusion welding to determine the nature and integrity of the welds.

The following are examples of practice of the invention employing the novel ultrasonic coupling composition hereof.

EXAMPLE 10

The composition of Example 1 above in the form of a thick gel was applied by brushing to selected areas of aluminum parts to form a thin layer of the gel on the part surface. Some of these parts had ridges while others were smooth parts. The transducer of an ultrasonic test equipment was pressed into contact with the surface of the gel on the respective parts and was moved by sliding in various selected directions over the gel along the surface of the parts. Variations in noise signals on the CRT display unit of the test equipment indicated cracks and discontinuities in the part, and presenting an indication of the location, orientation and size of very small as well as large cracks and flaws in the part.

The gel containing the fluorescent dye of Example 1, had a light yellow coloration but was transparent and the part surface could be viewed through the gel layer.

After testing was completed, the gel layer was removed from the parts by an air-water spray, the compositions so removed being biodegradable and sewered. The area from which the gel layer was removed was then viewed under fluorescent or black light, and residual gel on the surface was indicated by very bright fluorescent yellow-green smears. Such residual gel was then removed by a final water spray.

Excellent results were obtained in locating and detecting cracks on both the ridged and smooth parts. It has been found that parts containing ridges cannot be effectively ultrasonically inspected using prior art couplants.

EXAMPLE 11

The procedure of Example 10 above was essentially repeated, but employing as the test parts chromium-plated brass containing minute cracks of the order of 0.00002 to 0.0001 inch in width distributed over the surface of the parts, the parts being heated to about 300° F., the gel being applied to the part surfaces disposed in vertical position. The gel employed was the composition of Example 4, which was in the form of a thick gel.

The transducer was pressed into contact with the gel on the vertical surface of the parts, and was moved by sliding in various directions. The variations in noise signals produced by ultrasonic transmission generated by the transducer and transmitted through the test body were observed on the display unit of the ultrasonic test equipment, detecting the location, orientation and size of the cracks within the parts. During the inspection process, it was noted that the transducer could be positioned at any location on the gel disposed on the vertical surface of the part, and the transducer remained in this position without any support by the operator's hand, permitting the operator freedom to make adjustments on the test equipment at will.

Following inspection, the gel was scraped free of the surface of the part of a knife or similar means, and re-used, after which the part was viewed under black or fluorescent light, with residual traces of the gel indicated by bright yellow smears. The residual gel was then removed from the part surface by water spraying, and the sprayed residual gel was sewered.

EXAMPLE 12

The procedure of Example 10 was essentially followed but employing the gel composition of Example 2, which was applied by spatula on a surface of a steel casting. The gel layer was in the form of a clear colorless transparent gel under visible light, so that the surface of the casting could be seen through the gel layer.

Upon contact with and movement of an ultrasonic probe or transducer of an ultrasonic test equipment over the surface of the part by sliding contact of the probe with the gel surface, microcracks as well as cracks of substantially larger size both in the surface and within the body of the casting were detected by variations in the noise signals transmitted through the body of the part and received by the receiving unit of the test equipment.

After testing, the gel layer was scraped from the surface of the part and returned to the container of gel for reuse and residual gel was then removed by water spray, the discharged mixture being biodegradable and was sewered.

EXAMPLE 13

The procedure of Example 12 was substantially repeated, but employing the gel composition of Example 6, containing no dye.

In this example, particular care was taken to remove practically all of the gel following ultrasonic inspection, by an air-water spray, leaving essentially no residual gel on the surface of the part.

From the foregoing, it is seen that the invention provides a highly effective substantially biodegradable water washable ultrasonic couplant composition in the form of a gel, which is heat resistant and does not convert to a powder at high temperatures, is nonflammable and non-toxic, and which can be applied effectively to heated surfaces of parts positioned at various angles, without runoff or dripping, and which can be readily removed from a part surface by conventional washing. The couplant gels of the invention contain as essential components a single liquid vehicle in the form of certain biodegradable oxyalkylated alcohols, and a substantial proportion of a silica, preferably fumed silica. Such oxyalkylated alcohols are compatible with metals, are substantially non-volatile, biodegradable and have high flash point generally in excess of 400° F.

When employing the ultrasonic couplant of the invention, the transducer or search unit slides over the gel covered surface with much less "grabbing", and air bubbles are not trapped under the unit, often characteristic of prior art couplants. Since good coupling is easily maintained when using the couplant gel of the invention, calibration, scanning and evaluation can be accomplished more rapidly, reducing total inspection time.

The gel compositions of the invention can also have medical applications using ultrasonic transmission, since the couplant gels of the invention are nontoxic and lack solvents which would irritate the human skin, and are odor-free.

Although applicant's above copending application Ser. No. 580,442, now U.S. Pat. No. 4,049,568, discloses and claims a dye penetrant composition for use in non-destructive testing of an object, and comprising a biodegradable nonionic oxyalkylated surfactant of the type employed in the couplant composition of the present invention, and silica, the composition of my above application necessarily contains a dye, so that the dye penetrant remaining in the cracks and flaws in a part surface will provide colored traces for detection of such cracks and flaws when the object is viewed either under ordinary or fluorescigenous light.

On the other hand, the ultrasonic couplant gel composition of the present application requires only two essential components, namely the oxyalkylated surfactant and silica, and the resulting gel functions in an entirely different manner, that is as a medium for ultrasonic transmission of the transducer and body being subject to non-destructive testing, as contrasted to the function of the dye penetrant composition of my above application. As previously noted, any dye added to the couplant composition of the present invention is optional and is only used to check for completeness of couplant removal after the test.

It was unexpected to find that the dye penetrant gel composition of my above application, in the absence of the dye, could function in an entirely different manner as an effective couplant for ultrasonic inspection of objects, and have the advantageous properties of high heat stability, biodegradability and ability to remain on slanted and vertical surfaces without dripping, while at the same time having the ability to support a transducer placed on the gelled surface for easy sliding thereon, yet without "grabbing" and without unduly sticking to the transducer, and without trapping undesirable air bubbles.

While I have described particular embodiments of my invention for the purpose of illustration within the spirit of the invention, it will be understood that the invention is not to be taken as limited except by the scope of the appended claims.

What is claimed is:

1. A heat resistant biodegradable composition for ultrasonic inspection of surface and subsurface flaws and discontinuities in an object, in the form of a gel consisting essentially of (1) a biodegradable nonionic liquid surfactant as the sole liquid vehicle, said surfactant selected from the group consisting of (a) straight chain, primary, aliphatic oxyalkylated alcohols, wherein said alcohols can contain from 8 to 20 carbon atoms and the oxyalkyl groups are a mixture of ethylene oxide and propylene oxide groups, and (b) ethoxylates of linear secondary aliphatic alcohols, with the hydroxyl groups randomly distributed, the linear aliphatic portion of said alcohols being a mixture of alkyl chains containing in the range from 10 to 17 carbon atoms, and containing an average of from 3 to 12 moles of ethylene oxide, and (2) an amount of silica sufficient to convert said surfactant liquid into a gel.

2. An ultrasonic couplant composition as defined in claim 1, said silica being present in an amount ranging from about 4 to about 35% by weight of said composition.

3. An ultrasonic couplant composition as defined in claim 1, said silica being powdered silica present in an amount ranging from about 10 to about 25% by weight of said composition.

4. An ultrasonic couplant composition as defined in claim 3, wherein said silica is fumed silica.

5. An ultrasonic couplant composition as defined in claim 1, wherein said surfactant (a) is a mixture of compounds having the formula:

R—O(A)H wherein R is an essentially linear alkyl group having from 10 to 18 carbon atoms, at least 70 weight percent of said compounds in said mixture having an R of from 12 to 16 carbon atoms, and A is a mixture of oxypropylene and oxyethylene groups, said oxypropylene and oxyethylene groups being from 55 to 80% of the total weight of said compounds, the oxypropylene to oxyethylene ratio of said total weight being from 0.85:1 to 2.75:1; and wherein said surfactant (b) is ethoxylates of a mixture of alcohols having the formula:

$$CH_3-(CH_2)_n-CH_3$$
$$|$$
$$O-(CH_2-CH_2O)_m-H$$

where n is in the range from 9 to 13 and m is an average of 3 to 12.

6. An ultrasonic couplant composition as defined in claim 5, wherein R in said surfactant (a) can have from 12 to 18 carbon atoms, and the total number of A groups can range from about 4 to about 14; and wherein in surfactant (b) the linear alkyl hydrophobic portion of said surfactant is a mixture of $C_{11}$ to $C_{15}$ linear chains, and the hydrophilic portion of said surfactant is a polyoxyethylene chain randomly attached to the linear alkyl hydrophobic chains other than to the terminal carbon atoms, through the ether linkage, and wherein said surfactant (b) is selected from the group consisting of said ethoxylates of said mixture of alcohols, wherein n ranges from 9 to 13, and m is an average of 3, 5, 7, 9 or 12.

7. An ultrasonic couplant composition as defined in claim 6, said silica being present in an amount ranging from about 4 to about 35% by weight of said composition.

8. An ultrasonic couplant composition as defined in claim 6, said silica being powdered silica present in an amount ranging from about 10 to about 25% by weight of said composition.

9. An ultrasonic couplant composition as defined in claim 8, wherein said silica is fumed silica, said composition ranging from a thin to a heavy consistency, said composition being non-dripping.

10. An ultrasonic couplant composition as defined in claim 6, wherein said surfactant is said surfactant (b).

11. An ultrasonic couplant composition as defined in claim 10, wherein said silica is fumed silica, and said silica is present in an amount ranging from about 4 to about 35% by weight of said composition.

12. An ultrasonic couplant composition as defined in claim 11, wherein said silica is present in an amount ranging from about 10 to about 25% by weight of said composition.

13. An ultrasonic couplant composition as defined in claim 11, employing a combination of said biodegradable nonionic surfactants.

14. An ultrasonic couplant composition as defined in claim 11, employing a combination of said biodegradable nonionic surfactants wherein m in one of said surfactants is an average of 5 and m in another of said surfactants is an average of 9.

15. A method for detecting surface and subsurface flaws and discontinuities in an object, which comprises applying to a surface of said object a water washable biodegradable heat resistant ultrasonic couplant composition in the form of a gel which consists essentially of (1) a biodegradable nonionic liquid surfactant as the sole liquid vehicle, said surfactant selected from the group consisting of (a) straight chain, primary, aliphatic oxyalkylated alcohols, wherein said alcohols can contain from 8 to 20 carbon atoms and the oxyalkyl groups are a mixture of ethylene oxide and propylene oxide groups, and (b) ethoxylates of linear secondary aliphatic alcohols, with the hydroxyl groups randomly distributed, the linear aliphatic portion of said alcohols being a mixture of alkyl chains containing in the range from 10 to 17 carbon atoms, and containing an average of from 3 to 12 moles of ethylene oxide, and (2) an amount of silica sufficient to convert said liquid surfactant into a gel, contacting a transducer of an ultrasonic testing device with said gel on said surface of said object, and transmitting ultrasonic energy through said gel and into said object to inspect said object and locate any surface or subsurface flaws, cracks or discontinuities in said object, and removing said ultrasonic couplant composition from said surface.

16. A method as defined in claim 15, wherein said surface is a surface heated to elevated temperature and said silica is present in amount sufficient to prevent runoff when said surface is a slanted or vertical surface.

17. A method as defined in claim 15, said surface being heated to a temperature ranging from 150° F. to about 300° F.

18. A method as defined in claim 15, said silica being present in an amount ranging from about 4 to about 35% by weight of said composition.

19. A method as defined in claim 15, said silica being powdered silica present in an amount ranging from about 10 to about 25% by weight of said composition.

20. A method as defined in claim 19, said composition containing a fluorescent dye, and following removal of said composition from said object, inspecting said surface of said object under fluorescent light to detect any residual trace of said composition on said surface as indicated by fluorescent emission from said fluorescent dye in said composition.

21. A method as defined in claim 15, wherein said surfactant (a) is a mixture of compounds having the formula:

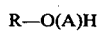

wherein R is an essentially linear alkyl group having from 10 to 18 carbon atoms, at least 70 weight percent of said compounds in said mixture having an R of from 12 to 16 carbon atoms, and A is a mixture of oxypropylene and oxyethylene groups, said oxypropylene and oxyethylene groups being from 55 to 80% of the total weight of said compounds, the oxypropylene to oxyethylene ratio of said total weight being from 0.85:1 to 2.75:1; and wherein said surfactant (b) is ethoxylates of a mixture of alcohols having the formula:

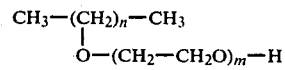

where n is in the range from 9 to 13 and m is an average of 3 to 12.

22. A method as defined in claim 21, wherein R in said surfactant (a) can have from 12 to 18 carbon atoms, and the total number of A groups can range from about 4 to about 14; and wherein in surfactant (b) the linear alkyl hydrophobic portion of said surfactant is a mixture of $C_{11}$ to $C_{15}$ linear chains, and the hydrophilic portion of said surfactant is a polyoxyethylene chain randomly attached to the linear alkyl hydrophobic chains other than to the terminal carbon atoms, through the ether linkage, and wherein said surfactant (b) is selected from the group consisting of said ethoxylates of said mixture of alcohols, wherein n ranges from 9 to 13, and m is an average of 3, 5, 7, 9 or 12.

23. A method as defined in claim 22, wherein said surface is heated to elevated temperature, said silica being present in an amount ranging from about 4 to about 35% by weight of said composition.

24. A method as defined in claim 22, said composition also including a fluorescent dye in an amount of about 0.1 to about 5% by weight, and said silica is fumed silica, employed in an amount ranging from about 10 to about 25% by weight of said composition, said composition ranging from a thin to a heavy consistency and being non-dripping, and following removal of said composition from said object, inspecting said surface of said object under fluorescent light to detect any residual trace of said composition on said surface as indicated by fluorescent emission from said fluorescent dye in said composition.

25. A method as defined in claim 24, wherein said surfactant is said surfactant (b), and said fluorescent dye is present in an amount of about 0.2 to about 2% by weight.

26. A method as defined in claim 24, said removing said ultrasonic couplant composition from said surface being carried out by a water wash.

27. A method as defined in claim 25, employing a combination of said surfactants wherein m in one of said surfactants is an average of 5 and m in another of said surfactants is an average of 9.

* * * * *